United States Patent [19]

Stemmler et al.

[11] 4,379,905

[45] Apr. 12, 1983

[54] PROCESS FOR THE PREPARATION OF POLYISOCYANATES CONTAINING ISOCYANURATE GROUPS AND THEIR USE IN THE PRODUCTION OF POLYURETHANES

[75] Inventors: Ingo Stemmler; Hanns P. Müller, both of Odenthal; Kuno Wagner, Leverkusen, all of Fed. Rep. of Germany

[73] Assignee: Bayer Aktiengesellschaft, Leverkusen, Fed. Rep. of Germany

[21] Appl. No.: 337,344

[22] Filed: Jan. 6, 1982

[30] Foreign Application Priority Data

Jan. 8, 1981 [DE] Fed. Rep. of Germany ....... 3100263

[51] Int. Cl.$^3$ .............................................. C08G 18/77
[52] U.S. Cl. ...................................... 528/73; 544/193; 544/222
[58] Field of Search ................... 528/73; 544/193, 222

[56] References Cited

U.S. PATENT DOCUMENTS

| | | | |
|---|---|---|---|
| 2,952,665 | 9/1960 | Bunge et al. | 260/77.5 |
| 3,252,942 | 5/1966 | France et al. | 260/77.5 |
| 3,330,828 | 7/1967 | Grogler et al. | 260/248 |
| 3,394,111 | 7/1968 | Liebsch | 260/77.5 |
| 3,686,225 | 8/1972 | Peperson | 260/340.3 |
| 3,919,218 | 11/1975 | Schmitt et al. | 260/248 NS |
| 4,115,373 | 9/1978 | Henes et al. | 528/48 |
| 4,196,289 | 4/1980 | Saito et al. | 544/221 |
| 4,252,923 | 2/1981 | König et al. | 525/452 |
| 4,255,569 | 3/1981 | Müller et al. | 544/193 |

FOREIGN PATENT DOCUMENTS

| | | |
|---|---|---|
| 10589 | 6/1980 | European Pat. Off. |
| 1013869 | 8/1957 | Fed. Rep. of Germany |
| 3006634 | 8/1981 | Fed. Rep. of Germany |
| 105813 | 9/1974 | German Democratic Rep. |
| 809809 | 3/1959 | United Kingdom |
| 952931 | 3/1964 | United Kingdom |
| 966338 | 8/1964 | United Kingdom |
| 1433642 | 4/1976 | United Kingdom |

OTHER PUBLICATIONS

J. H. Saunders and K. C. Frisch, *Polyurethanes, Chemistry and Technology*, pp. 94 et seq (1962).
A. Farkas and G. A. Mills, *Advances in Catalysis*, vol. 13, pp. 393 et seq (1962).
Houben-Weyl, vol. 8, p. 244, Thieme-Verlag.
J. E. Kresta, R. J. Chang, S. Kathiriya and K. C. Frisch, Makromol. Chem. 180, pp. 1081 et seq (1979).

*Primary Examiner*—Maurice J. Welsh
*Attorney, Agent, or Firm*—Gene Harsh; Lawrence S. Pope; Thomas W. Roy

[57] ABSTRACT

The subject of the invention is a process for the preparation of polyisocyanates containing isocyanurate groups which comprises trimerizing a proportion of the isocyanate groups of organic polyisocyanates or mixtures of di- and monoisocyanates in the presence of basic alkali metal compounds as catalysts and terminating the trimerization reaction by the addition of a catalyst poison, characterized in that the trimerization catalysts are complexes of (i) basic alkalimetal compounds and
(ii) acyclic organic compounds which
  (a) have at least 6 alkylene oxide units of the formula —R—O—, wherein R represents $C_1$–$C_4$-alkylene, in the form of one or more polyether chains with only those chains having at least three alkylene oxide units being counted to achieve the total of at least 6 alkylene oxide units
  (b) contain a total of at least about 40% by weight of alkylene oxide units, the alkylene oxide units of any chains containing less than three of these units not being counted as alkylene oxide units, and
  (c) have a molecular weight of at least about 282.

The invention also relates to the use of the process products according to the invention, optionally freed from excess starting polyisocyanates and/or optionally blocked with blocking agents for isocyanate groups, as an isocyanate component for the production of polyurethanes by the isocyanate polyaddition process.

12 Claims, No Drawings

PROCESS FOR THE PREPARATION OF POLYISOCYANATES CONTAINING ISOCYANURATE GROUPS AND THEIR USE IN THE PRODUCTION OF POLYURETHANES

BACKGROUND OF THE INVENTION

1. Field of the Invention

This invention relates to a process for the preparation of polyisocyanates containing isocyanurate groups by trimerizing a proportion of the isocyanate groups of organic polyisocyanates using novel trimerization catalysts and terminating of the trimerization reaction by the addition of a catalyst poison, and the use of the products obtained by the process according to the invention, optionally freed from monomeric starting polyisocyanate and/or blocked with blocking agents for isocyanate groups, as an isocyanate component in the production of polyurethanes.

2. Description of the Prior Art

Processes for the trimerization of organic isocyanates, in particular polyisocyanates, are known in large numbers (J. H. Saunders and K. C. Frisch, Polyurethanes Chemistry and Technology, page 94 et seq (1962)). Strong organic bases are suitable as catalysts for trimerization, e.g. those metal salts of carboxylic acids which are alkaline in action, metal alcoholates, metal phenolates, alkali metal carbonates, tertiary amines, tertiary phosphines and the "onium" compounds of nitrogen and phosphorus as well as basic heterocyclic compounds of these elements. The catalysts are frequently used in combination or together with other cocatalysts such as mono-N-substituted carbamic acid esters (A. Farkes and G. A. Mills, Advances in Catalysis, Volume 13, 393 (1962)). Elaborate catalyst systems are in most cases used since it is known that simple metal salts such as carboxylates or alcoholates are only capable of effecting cyclotrimerization of isocyanates if used at relatively high concentrations and at high temperatures (see e.g. British Pat. No. 809,809, Example 6).

If the trimerization with metal salts is to be carried out in a solvent, it is necessary to use highly polar aprotic solvents such as dimethyl formamide or dimethyl sulphoxide since only these are capable of dissolving inorganic metal salts and metal salts with a small organic group (German Offenlegungsschrift No. 2,839,084). Even then, catalyst concentrations of from 0.1 to 0.5% by weight are required. This also applies if the solvents used are protic solvents but react with the isocyanate to form urethanes and thus lower the isocyanate content or form precipitates and cloudiness so that the reaction product must be filtered (British Pat. No. 920,080).

Furthermore, the metal salts used in the state of the art effect rapid trimerization only in the case of aromatic isocyanates while aliphatic mono and polyisocyanates require a high catalyst concentration and comparatively high temperatures which frequently result in an uneven exothermic reaction, and in the case of polyisocyanates lead to the formation of highly viscous, strongly discolored products (see U.S. Pat. No. 3,330,828, Examples 1 to 4; British Pat. No. 952,931, Example 3; German Auslegeschrift No. 1,013,869, Example 3) or the formation of gel particles (British Pat. No. 966,388, Example 3) with the result that the products are not suited as isocyanate components for high quality polyurethane lacquers. One serious disadvantage of metal salt catalysis is also to be seen in the fact that when catalysis is stopped, e.g. by the addition of acid compounds, inorganic salts are formed which are insoluble in the polyisocyanate and cause cloudiness. In the more recent processes of the state of the art, therefore, special organic bases are used as trimerization catalysts. Thus, for example, Mannich bases (German Offenlegungschrift No. 2,551,634 and German Offenlegungsschrift No. 2,641,380) or tertiary phosphines are used for the trimerization of aromatic polyisocyanates. In the case of phosphines, uretdiones are first formed which then react to form the isocyanurate in a second reaction phase (German Offenlegungsschrift No. 1,201,992). For the trimerization of (cyclo) aliphatic diisocyanates there have recently in many cases been used organic bases with a betaine structure such as quaternary ammonium hydroxides (European Application Nos. 010,589 and 009,694), aminimides (J. E. Kresta, R. J. Chang, S. Kathiriya and K. C. Frisch, Makromol. Chem. 180, 1081 (1979)) and aziridine derivatives in combination with tertiary amines (German Auslegeschrift No. 2,325,826).

All of these catalyst systems have the disadvantage that quite specific temperature intervals must be observed and in some cases the process must be carried out solvent free. In others, the process may only be conducted in selected solvents, and in still others trimerization may be carried out either on aromatic polyisocyanates alone or on aliphatic polyisocyanates alone.

It is therefore an object of the present invention to provide a process by which colorless polyisocyanates containing isocyanurate groups, both those with an aromatic and those with an aliphatic structure, may be prepared by a technically simple procedure with one and the same catalyst, either with or without solvent and without elaborate temperature control.

This problem was surprisingly able to be solved by the process according to the invention described below, in which novel trimerization catalysts are used.

SUMMARY OF THE INVENTION

The subject of the invention is a process for the preparation of polyisocyanates containing isocyanurate groups which comprises trimerizing a proportion of the isocyanate groups of organic polyisocyanates or mixtures of di- and monoisocyanates in the presence of basic alkali metal compounds as catalysts and terminating the trimerization reaction by the addition of a catalyst poison, characterized in that the trimerization catalysts are complexes of (i) basic alkalimetal compounds and
(ii) acyclic organic compounds which
 (a) have at least 6 alkylene oxide units of the formula —R—O—, wherein R represents $C_1$–$C_4$-alkylene, in the form of one or more polyether chains with only those chains having at least three alkylene oxide units being counted to achieve the total of at least 6 alkylene oxide units,
 (b) contain a total of at least about 40% by weight of alkylene oxide units, the alkylene oxide units of any chains containing less than three of these units not being counted as alkylene oxide units, and
 (c) have a molecular weight of at least about 282.

The invention also relates to the use of the process products according to the invention, optionally freed from excess starting polyisocyanates and/or optionally blocked with blocking agents for isocyanate groups, as an isocyanate component for the production of polyurethanes by the isocyanate polyaddition process.

DETAILED DESCRIPTION OF THE INVENTION

The novel complexes to be used as trimerization catalysts in the process according to the invention are those based on (i) basic alkalimetal compounds and (ii) certain organic compounds having polyether segments.

As catalyst component (i) there may be used any basic alkalimetal compounds, i.e. in particular those which in a 1 molar concentration in aqueous solution result in a pH of the solution of at least about 7.5. These are generally compounds of sodium, potassium, rhubidium or cesium conforming to this definition, sodium and potassium compounds being preferred. Lithium compounds are less preferred.

Typical examples of basic alkalimetal compounds suitable as catalyst component (i) are the hydroxides; carbonates; cyanates; cyanides; carboxylates (with 1 to 18 carbon atoms) such as e.g. formates, acetates, propionates, 2-ethyl-hexanoates, stearates, oleates, benzoates, naphthenates, or caproates; alcoholates (with 1 to 6 carbon atoms) such as methylates, ethylates or butylates; phenolates (with 6 to 10 carbon atoms); enolates such as acetylacetonates or acetoacetic stearates; or addition products of the above-mentioned alkalimetals with acid amides such as acetic acid amide. The carboxylates are preferred.

The catalyst components (ii) are acyclic organic compounds fulfilling the criteria mentioned under (a) to (c) above, in particular those which (a) have at least 7 alkylene oxide units of the type mentioned, preferably ethylene oxide and optionally propylene oxide units in the form of one or more polyether chains with only those chains having at least 3, preferably at least 7 alkylene oxide units, being counted to achieve the total of at least 7 alkylene oxide units, (b) contain at least about 55% by weight of alkylene oxide units of the type mentioned built into polyether chains, the alkylene oxide units of any chains containing less than three of these units not being counted as alkylene oxide units, and wherein at least about 50%, preferably at least about 80% of all the alkylene oxide units present are ethylene oxide units, and (c) have a molecular weight of about 282 to 3,000, most preferably about 326 to 1,000.

Typical examples of suitable catalyst components (ii) are polyether alcohols with a valency of 1 to 3 conforming to these definitions, such as may be obtained in known manner by the alkoxylation, in particular ethoxylation, of suitable starter molecules, for example monohydric alcohols such as methanol, ethanol, n- or i-propanol, n-, i-, sec- or tertiary butanol, or water; or starter molecules with a valency of at least 2, such as ethylene glycol, propane diol-(1,2), propane diol-(1,3), butane diols, pentane diols or hexane diols, glycerol, trimethylol ethane or trimethylol propane. Also suitable are those polyethers of the type mentioned by way of example in which the hydroxyl end group or groups has or have been blocked for example by alkylation, acylation and/or urethanization, so that no end groups having an isocyanate reactivity comparable to that of hydroxyl groups are left, or derivatives of the above-mentioned polyether alcohols which have been chain lengthened by reaction with chain lengthening agents, for example diisocyanates such as tetramethylene diisocyanate, hexamethylene diisocyanate or 2,4-diisocyanatotoluene, provided the derivatives obtained conform to the definitions stated above.

Blocking of the hydroxyl end group(s) of the polyether alcohols exemplified above by alkylation is carried out by, for example, reaction of the polyether alcohols with alkylating agents such as e.g. dimethyl sulphate, $C_1$–$C_4$ alkyl halides or benzyl halide; blocking by an acylating reaction is carried out by a reaction with acylating agents such as e.g. acetic acid anhydride, acetyl chloride or benzoyl chloride; blocking by urethanization is carried out by reaction with monovalent isocyanates such as e.g. methyl, ethyl, hexyl or phenylisocyanate. Methylene oxide units, optionally substituted, are introduced into the polyether by reaction of the polyether alcohols exemplified above with aldehydes such as formaldehyde, acetaldehyde or benzaldehyde in the sense of an acetalization.

To prepare the complexes to be used as trimerization catalysts, which are an essential feature of the invention, components (i) and (ii) mentioned by way of example or any mixtures thereof are reacted together in such quantitative proportions that from about 0.8 to 2.0, preferably from about 1.0 to 1.5 mol of compounds (ii) conforming to the above definitions are available for each gram equivalent of basic metal compound (i). If, in the preparation of the complexes, the alkoxylation products of the starter molecules exemplified above or of their derivatives constitute mixtures owing to the statistical course of the alkoxylation reaction, and these mixtures, in addition to containing compounds (ii) conforming to the above definitions also contain compounds which do not conform to these definitions, for example because they do not contain sufficient alkylene oxide units, then the quantity of such mixtures must, of course, be calculated so that the above proportions of components (i) and (ii) are observed. The reaction between components (i) and (ii), i.e. the complex formation, generally takes place spontaneously at a temperature of about 10° to 60° C., particularly if components (i) and (ii) are compatible with each other and are used in the absence of solvents. The formation of complexes may, however, also be carried out in the presence of solvents or solvent mixtures. Examples of suitable solvents are: methanol, ethanol, propanol, ethylene glycol, propane diol-(1,2), propane diol-(1,3), butylene glycol, glycerol or oligoethylene- or -propylene glycols (degree of oligomerization 2 to 6). The alcohols should on the one hand readily dissolve the metal compounds, but on the other hand still be miscible to some extent with the isocyanate and have a low viscosity.

Aprotic solvents which are unreactive with isocyanates may also be used, with an $E_T$ value (Cr. Reichardt, Lösungsmittel-Effekte in der organischen Chemie, Chem. Taschenbücher Volume 4, Verlag Chemie 196) preferably in the range of about 33.5 to 47. Examples include nitriles such as acetonitrile, propionitrile or benzonitrile; nitro compounds such as nitro methane or nitro benzene; carbonic acid esters such as ethylene or propylene carbonate; and ketones such as acetone, acetophenone, butyl methyl ketone or isobutyl methyl ketone. There may even be used such apolar solvents as chlorinated hydrocarbons, e.g. methylene chloride, chloroform, 1,1,1-trichloroethane or trichloroethylene; aromatic hydrocarbons such as benzene, toluene or xylene; or esters such as ethyl acetate, butyl acetate or ethylene glycol monomethyl ether acetate.

Although strongly polar solvents such as dimethyl formamide, N-methyl pyrrolidone, tetramethyl urea or dimethyl sulphoxide may also be used in principle, they are not to be recommended, firstly because they are difficult to free from by-products such as amines and secondly because they generally catalyze undesirable side reactions of isocyanate groups so that the process products according to the invention would not be stable in storage in the presence of such solvents.

Auxiliary aprotic solvents of the type exemplified above are generally used when components (i) and (ii) are incompatible or only poorly compatible with each other. If components (i) and (ii) are compatible with each other and/or readily soluble in the solvent used, mixtures of (i) and (ii) or solutions thereof may be used as trimerization catalysts immediately after their preparation. If, however, components (i) and (ii) are not compatible with each other and insoluble or only difficulty soluble in the solvent used, it is often advisable to subject the suspension initially formed to a process of mechanical mixing for about 15 to 360 minutes within the temperature range mentioned and to filter off any precipitate remaining. The solution of the complex then obtained may be used as such or concentrated by evaporation under vacuum. The solvent free complex left behind may finally be dissolved in other, preferably aprotic solvents. In this way, for example, about 0.2 molar "solutions of potassium acetate" in toluene may be prepared at room temperature.

When carrying out the process according to the invention, it is not necessary to observe strict absence of alcohol in solvents for the complexes or of hydroxyl group-containing complex formers (ii) since the extremely small quantities of the isocyanate-reactive groups in question are negligible compared with the isocyanate groups of the starting polyisocyanate which is to be trimerized.

The essential trimerization catalysts of the invention thus obtained may, of course, be used for the preparation of any isocyanurates. This means that the catalysts are suitable not only for the process according to the invention but also, for example, for the preparation of isocyanurates by the trimerization of monoisocyanates.

In the process according to the invention, the complex catalysts which are essential to the invention are used as individual components or as preformed complexes, as already mentioned above, solvent free or as about 0.005 to 95, preferably about 0.01 to 70% by weight solutions in the solvents exemplified. When hydroxyl-containing solvents or complex formers (ii) with free hydroxyl groups are used, the process according to the invention gives rise to urethane groups due to the reaction with a portion of the isocyanate groups in the starting polyisocyanate. This is often desirable since such urethane groups have a cocatalytic effect. The quantity of such solvents, if they are monohydric alcohols, and of complex formers should, however, be limited so that the reaction mixture contains at the most about 2 mol % of hydroxyl groups, based on the quantity of isocyanate groups of the starting polyisocyanate. It is often suitable to use polyhydric alcohols such as e.g. ethylene glycol or glycerol as hydroxyl group-containing solvents for the essential complexes for the invention in order that the isocyanate functionality of the process products according to the invention will not be reduced by urethane formation. The quantity of such polyhydric alcohols must, of course, be limited so as not to give rise to any polyurethanes which are difficulty soluble in the process products.

In the process according to the invention, the complexes which are essential to this invention are generally used in quantities of from about 0.001 to 0.5, preferably from about 0.001 to 0.1 mol %, based on the alkali metal compound (i) on the one hand and the starting polyisocyanate to be trimerized on the other hand. If aromatic polyisocyanates are trimerized in the process according to the invention without the use of solvents, the quantity of the essential catalysts according to the invention is preferably within the range of from about 0.001 to 0.02 mol % whereas if the aromatic starting polyisocyanate is diluted with a suitable aprotic solvent, the quantity of the complex is generally from about 0.01 to 0.08 mol %. If the starting polyisocyanates used have exclusively aliphatically bound isocyanate groups, the quantity of the catalyst is generally within the range of from about 0.01 to 0.1 mol %, whereas, if starting polyisocyanates with cycloaliphatically bound isocyanate groups are used the quantity of catalyst used is preferably from about 0.03 to 0.5 mol %, all percentages being based on the alkali metal compound (i) on the one hand and the starting polyisocyanate on the other.

Any organic polyisocyanates may be used as starting materials in the process according to the invention. The process according to the invention is suitable in particular for the partial trimerization of the isocyanate groups of diisocyanates with molecular weights in the range of about 140 to 300 which have aromatically, aliphatically or cycloaliphatically bound isocyanate groups, such as e.g. tetramethylene diisocyanate, hexamethylene diisocyanate, 1-isocyanato-3,3,5-trimethyl-5-isocyanatomethyl-cyclohexane (isophorone diisocyanate, abbreviated: IPDI), 2,4- and/or 2,6-diisocyanatotoluene, 2,4'- and/or 4,4'-diisocyanatodiphenyl methane, 2,4'-diisocyanatodicyclohexyl methane, 1-methyl-2,4-diisocyanato-cyclohexane, lysine ester diisocyanates, p-xylylene diisocyanate or any mixtures of such diisocyanate. Particularly suitable are also mixtures of the aromatic diisocyanates exemplified above with the exemplified aliphatic diisocyanates in proportions by weight of from about 1:3 to 3:1. Higher functional polyisocyanates such as, for example, polyisocyanate mixtures formed by the phosgenation of aniline/formaldehyde condensates may also be used as starting polyisocyanates in the process according to the invention. It is also possible in principle, although less preferred, to use isocyanate prepolymers, i.e., reaction products of excess quantities of the diisocyanates mentioned as examples with at least difunctional compounds having isocyanate reactive groups as starting polyisocyanates in the process according to the invention. Mixtures of diisocyanates and monoisocyanates may in principle also be used as starting materials in the process according to the invention in order to obtain interesting polyisocyanate containing isocyanurate groups in which the isocyanate functionality is reduced by a controlled amount. In this case, the di- and monoisocyanates are generally used in a molar ratio of diisocyanate:monoisocyanate in the range of about 1.5:1 to 2.5:1. Suitable monoisocyanates are, for example, aliphatic monoisocyanates having 1 to 18, preferably 4 to 8 carbon atoms, such as methyl isocyanate, n-butyl isocyanate, n-octylisocyanate or stearylisocyanate or aromatic monoisocyanates, in particular phenyl isocyanate. Preferred starting polyisocyanates for the process according to the invention are: 2,4- and/or 2,6- diisocyanatotoluene, hexamethylene diisocyanate and IPDI.

The process according to the invention may be carried out in the absence or presence of solvents which are inert towards isocyanate groups. Suitable solvents for the process according to the invention are any solvents or solvent mixtures within a wide range of melting points of about 50° C./1013 mbar to about 250° C./13.3 mbar which are inert towards isocyanate groups. Low to medium boiling solvents or high boiling solvents may be used, depending on the field of application of the process products according to the invention. Preferred solvents to be used are, for example, esters such as ethyl acetate, butyl acetate, ethylene glycolmonomethyl ether acetate, ethylene glycol-monoethyl ether acetate or ketones such as e.g. acetone, methyl ethyl ketone, methyl isobutyl ketone, cyclohexanone or methoxy hexanone. Phthalic acid esters, such as dibutyl phthalate or butyl benzyl phthalate, or phosphoric acid esters such as tricresyl phosphate, or alkyl sulphonic acid esters of phenol and of cresol are also suitable. In diluents such as toluene, xylene or higher aromatic compounds there is frequently only limited solubility so that larger additions of such diluents may lead to cloudiness and precipitations in the reaction products.

The solvent used for carrying out the process according to the invention and the quantity of solvent used need not be identical to the solvent or quantity of solvent present in the process products according to the invention when they are used according to the invention. Thus after completion of the process according to the invention, the solvent or solvent mixture used may, of course, be completely or partly removed by distillation and completely or partly replaced by another solvent. Products which have been prepared solvent-free may, of course, subsequently be dissolved in the above-mentioned solvents.

The process according to the invention is generally carried out in the temperature range of from about 0° to 200° C., preferably from about 10° to 100° C. and most preferably from about 25° to 80° C. If the process according to the invention is carried out in the presence of a solvent, the starting polyisocyanate to be trimerized and the particular solvent are generally used in quantities corresponding to a proportion by weight in the range of about 1:4 to 4:1, preferably about 1:2 to 2:1, most preferably about 0.8:1.2 to 1.2:0.8.

The catalyst quantity to be chosen depends, as described above, on the nature of the starting polyisocyanate and, of course, also on the reaction temperature at which the trimerization is to be carried out. It can be reliably determined by a simple investigative preliminary test. The catalyst concentration should generally be increased by a factor of about 6 to 10 when using solvents compared with that used in the solvent-free process.

The trimerization reaction may be carried out, for example, according to the following variations:
1. The catalyst or its solution in a suitable solvent is added to the polyisocyanate to be trimerized at room temperature without the addition of an auxiliary solvent for the trimerization reaction. The weakly exothermic trimerization reaction thereupon generally starts spontaneously. The reaction temperature is then maintained at the desired level, optionally by external cooling or heating, until the trimerization reaction is stopped by the addition of a catalyst poison.
2. The polyisocyanate to be trimerized is supplied in a solvent of the type exemplified above. To this solution is then added the trimerization catalyst or its solution. Depending on the nature of the starting polyisocyanate and of the trimerization catalyst, the trimerization reaction in this variation starts within an incubation period of about 0 to 180 minutes at room temperature or slightly elevated temperature. Such an incubation period is observed in particular if the process is carried out in the absence of hydroxyl group-containing solvents for the trimerization catalyst and in the absence of hydroxyl group-containing complex formers (ii). In this variation of the process according to the invention, the temperature of the reaction mixture is also adjusted within the above-mentioned ranges, optionally by external cooling or heating. Here again the trimerization reaction is stopped by the addition of a catalyst poison when the desired degree of trimerization is reached.
3. A previously prepared complex or its solution is first dissolved in the auxiliary solvent serving as reaction medium, whereupon the starting polyisocyanate to be trimerized is added. The subsequent procedure according to this variation is similar to that of the embodiment mentioned under 2. above.
4. Catalyst components (i) and (ii) are fed separately into the solvent serving as reaction medium. After intimate mixing, the starting polyisocyanate to be trimerized is added to the resulting complex solution. The subsequent reaction procedure according to this variation is also similar to that mentioned under 2.

In all the variations exemplified above of the process according to the invention, the trimerization reaction is generally stopped when a degree of trimerization (degree of trimerization=percentage of trimerized isocyanate groups based on the total quantity of isocyanate groups in the starting polyisocyanate) of about 10 to 70% is reached. If the process according to the invention is carried out solvent-free and excess starting polyisocyanate is subsequently removed, for example in a thin layer evaporator, the degree of trimerization is generally from about 10 to 40%. If the process according to the invention is carried out in the presence of solvents without subsequent removal of unreacted starting polyisocyanate, the degree of trimerization is generally from about 50 to 70%.

Suitable catalyst poisons are, for example, any acid halides, in particular acid chlorides, such as e.g. acetyl chloride, benzoyl chloride, terephthaloyl diol, phthaloyl dichloride, trichloroacetyl chloride, phosphorus trichloride or phosphorus tribromide or strong acids which neutralize the catalyst component (i) and thereby inactivate it, such as e.g. sulphuric acid, phosphoric acid, hydrogen chloride, toluene sulphonic acid, methane sulphonic acid, chlorosulphonic acid or nonafluorobutane sulphonic acid. To inactivate the catalyst, it is sufficient to add to the reaction mixture, based on the catalyst component (i), about 100 to 110 equivalent %, i.e. in the case of monofunctional catalyst poisons, about 100 to 110 mol % of the catalyst poison.

In order to prevent the formation of peroxides from the complex ligands (ii) in the event of prolonged storage, it is advisable to add suitable anti-oxidants to the process products according to the invention. Besides phenols or substituted phenols, which generally react with the isocyanate groups of the isocyanate, any other antioxidants of the state of the art known from polyurethane chemistry may be used. These antioxidants are generally added in a quantity of about 5 to 50% by weight, based on the quantity of the complex former (ii).

Particularly if the process according to the invention is carried out solvent-free, the process products according to the invention may be freed from excess unreacted starting polyisocyanate in known manner, for example by thin layer distillation, so that polyisocyanates having isocyanurate groups and containing less than about 3% by weight, preferably less than about 0.7% by weight of monomeric starting diisocyanates may be obtained.

The process products according to the invention may, of course, be blocked in known manner with suitable blocking agents for isocyanate groups, such as e.g. phenol, ε-caprolactam, diethyl malonate or ethyl acetoacetate.

The process products according to the invention and their derivatives obtained by the aforesaid blocking reaction are valuable starting materials for the production of polyurethanes when reacted with an isocyanate-reactive component by the isocyanate polyaddition process. They are suitable in particular as isocyanate components in two-component polyurethane lacquers.

The process according to the invention is distinguished from the known processes for the preparation of polyisocyanates having isocyanurate groups by the following advantages:

1. Only extremely small quantities of alkali metal compounds are used as catalysts.
2. The reaction is brought to a standstill by small quantities of catalyst poisons (acid chlorides, imidoyl chlorides or protonic acids). No precipitations of salts are observed under these conditions.
3. As regards the technical aspects of safety and of procedure, the weakly exothermic reaction may easily be controlled both continuously and discontinuously.
4. The reaction times are short.
5. The process products are colorless to slightly yellowish, transparent and stable in storage. Compared with those known in the art, liquid products have comparable or lower viscosities, solid products (e.g. from IPDI) have comparable or lower melting points.

The following examples explain the invention. All percentages refer to percentages by weight unless explicitly stated otherwise.

EXAMPLE 1

A solution of 0.0025 g (0.0025 mol %) of potassium acetate and 0.015 g of polyethylene glycol dimethyl ether (molecular weight 410) in 0.0325 g of ethanol is mixed at 23° C. with 174 g of tolylene diisocyanate (65% 2,4- and 35% 2,6-isomer). The temperature in the reaction mixture which is insulated against heat losses rises to 50° C. within 105 minutes and is then maintained at 50° C. by external cooling. After a total reaction time of 2 hours, the reaction is stopped by the addition of 0.004 g of acetyl chloride. The product has an isocyanate content of 41.6%. By removal of the monomeric tolylene diisocyanate by distillation in a thin layer evaporator in an oil pump vacuum, a pale yellow solid which is soluble in butyl acetate is obtained.

EXAMPLE 2

A solution of 0.02 g of sodium acetate (0.025 mol %) and 0.15 g of polyethylene glycol (average molecular weight 380) in 0.33 g of ethanol is added to 174 g of tolylene diisocyanate (65% 2,4- and 35% 2,6-isomer) at 25° C. with stirring. The temperature rises to 40° C. within 90 minutes and is maintained at 40° C. by cooling, later by heating. After a total reaction time of 105 minutes, trimerization is stopped at 41.6% isocyanate content by the addition of 0.08 g of acetyl chloride followed by 30 minutes stirring.

EXAMPLE 3

A solution of 0.02 g of potassium acetate (0.02 mol %) in 0.18 g of polyethylene glycol (average molecular weight 380) and 174 g of distilled 2,4-tolylene diisocyanate are added at 25° C. to 174 g of butyl acetate. The exothermic reaction starts at once, the reaction temperature rises to 40° C. in 5 minutes. The temperature is maintained at 40° C. by cooling or heating. After a reaction time of 2 hours, the reaction is stopped at an isocyanate content of 7.8% by the addition of 0.04 g of acetyl chloride. Stirring is carried out for a further 60 minutes at 40° C. The colorless, low viscosity solution still contains 0.6% of monomeric tolylene diisocyanate.

EXAMPLE 4

Example 3 is repeated but the reaction temperature is maintained at 30° C. by cooling or mild heating. After a reaction time of 3.5 hours, stopping of the reaction by the addition of 0.04 g of acetyl chloride and subsequent 60 minutes stirring, a colorless, low viscosity solution having an isocyanate content of 8.2% is obtained.

EXAMPLE 5

174 g of butyl acetate, a solution of 0.046 g of sodium phenolate (0.04 mol %) in 0.414 g of polyethylene glycol (average molecular weight 380) and 174 g of 2,4-tolylene diisocyanate are stirred together at 25° C. After an incubation time of 2.5 hours, the cyclotrimerization reaction starts up in the reaction vessel which is insulated against heat loss. The temperature in the reaction mixture is 28° C. after a total of 3.5 hours from the initial mixing step, 34° C. after 4 hours and 43° C. after 4.25 hours. The temperature is maintained at 40° C. by cooling. After a total reaction time of 5 hours, the reaction is stopped by the addition of 0.034 g of acetyl chloride. The liquid product still contains 8.2% by weight NCO.

EXAMPLES 6 to 13

The procedure is as in Example 3. For experimental details, see Table 1.

TABLE 1

Trimerization of 174 g of 2,4-tolylene diisocyanate in 174 g of butyl acetate with potassium acetate.

| Example Number | Potassium Acetate (g) | Complex Ligand Type | Quantity (g) | Cosolvent Type | For catalyst & Ligand Quantity (g) | Reaction Time (h) | Reaction Temperature (°C.) | Product: Isocyanate Content (% by weight) |
|---|---|---|---|---|---|---|---|---|
| 6 | 0.018 | A$^{(1)}$ | 0.071 | — | — | 12 | max 50 | 8.2 |
| 7 | 0.03 | B2$^{(2)}$ | 0.18 | EtOH$^{(8)}$ | 0.39 | 4 | 60 | 8.1 |
| 8 | 0.02 | C$^{(3)}$ | 0.16 | EtOH$^{(8)}$ | 0.22 | 7 | 50 | 8.2 |

TABLE 1-continued

Trimerization of 174 g of 2,4-tolylene diisocyanate in 174 g of butyl acetate with potassium acetate.

| Example Number | Potassium Acetate (g) | Complex Ligand Type | Quantity (g) | Cosolvent Type | For catalyst & Ligand Quantity (g) | Reaction Time (h) | Reaction Temperature (°C.) | Product: Isocyanate Content (% by weight) |
|---|---|---|---|---|---|---|---|---|
| 9  | 0.03 | D[(4)] | 0.31 | EtOH[(8)] | 0.26 | 7    | 50 | 8.2 |
| 10 | 0.02 | E[(5)] | 0.12 | EtOH[(8)] | 0.26 | 1    | 50 | 8.2 |
| 11 | 0.01 | E[(5)] | 0.06 | EtOH[(8)] | 0.13 | 10   | 40 | 8.1 |
| 12 | 0.02 | F[(6)] | 0.12 | MeOH[(9)] | 0.26 | 1.25 | 50 | 8.1 |
| 13 | 0.02 | G[(7)] | 0.18 | —         | —    | 2½   | 50 | 8.2 |

[(1)]Octaethylene glycol dimethyl ether;
[(2)]Dimethyl ether of polyethylene glycol (molecular weight 380);
[(3)]Dimethyl ether of polyethylene glycol (molecular weight 606);
[(4)]Trimethyl ether of polyether (from trimethylol propane and ethylene oxide, molecular weight 673);
[(5)]Bis-urethane from 2 mol of methyl isocyanate and 1 mol of polyethylene glycol (molecular weight 380);
[(6)]Polyether alcohol from butanol and ethylene oxide (molecular weight 515);
[(7)]Polyethylene glycol with average molecular weight 380);
[(8)]Ethanol;
[(9)]Methanol.

EXAMPLE 14

A solution of 50 mg of potassium acetate (0.017 mol) and 300 mg of a polyether based on butanol/ethyloxide (molecular weight 515) in 650 mg of methanol is added at 24° C. to 504 g of pure hexamethylene diisocyanate. The reaction starts up immediately without an induction period. A temperature of 58° C. is reached within 3 hours in the reaction mixture which is insulated against heat losses. After a total duration of 4.5 hours, the reaction is stopped by the addition of 0.08 g of acetyl chloride (0.001 mol) followed by 30 minutes stirring at 55° C. The crude isocyanurate-containing product still contains 41.1% NCO. After distillation in a thin layer evaporator under nitrogen at 0.5 Torr and 160° C., 170 g of colorless, low viscosity product having an isocyanate content of 22.2% and containing 0.7% of monomeric hexamethylene diisocyanate are obtained.

EXAMPLE 15

A solution of 0.96 g of potassium acetate ($9.8 \times 10^{-3}$ mol = 0.04 mol %) in 8.64 g of polyethylene glycol (average molecular weight 380) is added to 4032 g of distilled hexamethylene diisocyanate (24 mol) at 25° C. The temperature of the reaction mixture rises to 51° C. within 40 minutes and to 60° C. after a further 60 minutes. The temperature is then maintained at 60° C. After a total reaction time of 4.5 hours, trimerization is stopped by the addition of 1.0 g of acetyl chloride followed by 60 minutes stirring at room temperature.

The crude product has an isocyanate content of 40.8%. After removal of the monomeric hexamethylene diisocyanate by high vacuum distillation in a thin layer evaporator, 1350 g of a low viscosity product of $\eta(25°$ C.$) = 2,500$ mPas are obtained. The isocyanate content is 22.6%, the content in monomeric hexamethylene diisocyanate is 0.11%.

EXAMPLE 16

A solution of 0.96 g of potassium acetate in 8.64 g of polyethylene glycol (molecular weight 380) is added with stirring to 4032 g of pure hexamethylene diisocyanate (24 mol) at 25° C. The weakly exothermic reaction starts up at once and the temperature in the reaction mixture rises to 63° C. within 20 minutes. The reaction temperature is maintained at 60° C. by occasional cooling and, after a total reaction time of 75 minutes, the reaction is stopped at an isocyanate content of 40.5% NCO by the addition of 1.0 g of acetyl chloride. After high vacuum distillation in a thin layer evaporator, the pale yellow product (1,400 g) has a viscosity of 2,800 mPas/25° C. at an isocyanate content of 22.9% and a content in monomeric hexamethylene diisocyanate of 0.2%.

EXAMPLES 17 to 20

The procedure is the same as in Example 14. For experimental details see Table 2.

TABLE 2

Cyclotrimerization of 504 g of hexamethylene diisocyanate (3 mol) solvent-free with potassium acetate.

| Example Number | Potassium acetate (g) | Complex Ligand Type | Quantity (g) | Cosolvent Type | For catalyst & ligand quantity (g) | Reaction time (h) | Reaction Temperature (°C.) | Crude product NCO content (% by weight) |
|---|---|---|---|---|---|---|---|---|
| 17 | 0.25[(1)] | B      | 1.97 | CH$_2$Cl$_2$[(2)] | 350[(2)] (250ml) | 12  | 40–50 | 40.7 |
| 18 | 0.05      | B      | 0.3  | EtOH             | 0.65             | 5   | 50    | 41.1 |
| 19 | 0.05      | H[(3)] | 0.3  | EtOH             | 0.65             | 8   | 50–55 |      |
| 20 | 0.3       | F      | 1.8  | MeOH             | 3.9              | 1.5 | 60    | 41.1 |

[(1)]Potassium acetate, B vigorously stirred with 250 ml CH$_2$Cl$_2$ for 2 hours, filtered off, solution used;
[(2)]Distilled off under vacuum at beginning of reaction;
[(3)]Bis-urethane from 2 mol phenyl isocyanate and 1 mol G.

EXAMPLE 21

A solution of 0.3 g of potassium acetate (0.3 mol %) in 2.7 g of polyethylene glycol (molecular weight 380) is added to 222 g of isophorone diisocyanate (IPDI, 1 mol) with stirring at 60° C. After an initial cloudiness, the reaction mixture clears up in the course of the reaction. Stirring is continued for 18 hours at 60° C. Cyclotrimerization is then stopped at an isocyanate content of 30.2% by the addition of 0.26 g of acetyl chloride followed by 1 hour stirring at 60° C.

After removal of the monomeric IPDI by distillation in a thin layer evaporator at 160° C. and 0.1 Torr, a light yellow solid containing 0.5% monomeric IPDI and having a melting range of 121° to 127° C. is obtained.

What is claimed is:

1. A process for the preparation of polyisocyanates containing isocyanurate groups which comprises trimerizing a proportion of the isocyanate groups of organic polyisocyanates or mixtures of polyisocyanates and monoisocyanates in the presence of basic alkali metal compounds as catalysts and stopping the trimerization reaction by the addition of a catalyst poison, characterized in that the trimerization catalyst is a complex of
(i) a basic alkali metal compound and
   (ii) an acyclic organic compound which
   (a) has at least 6 alkylene oxide units of the formula —R—O, wherein R represents $C_1$-$C_4$ alkylene, in the form of one or more polyether chains with only those chains having at least 3 alkylene oxide units being counted to reach the total of at least 6 alkylene oxide units
   (b) contains a total of at least about 40% by weight of alkylene oxide units, the alkylene oxide units of any chains containing less than three of these units not being counted as alkylene oxide units, and
   (c) has a molecular weight of at least 282.

2. The process according to claim 1, characterized in that component (ii) comprises at least one compound with a molecular weight range of about 326 to 1,000 having at least 7 alkylene oxide units linked together in the form of a polyether chain, wherein at least about 80% of said alkylene oxide units are ethylene oxide units, and the remainder are propylene oxide units.

3. The process according to claim 2, characterized in that component (ii) comprises at least one monovalent or higher valent polyether alcohol.

4. The process according to claim 2 or 3, characterized in that component (i) comprises a sodium or potassium carboxylate having 1 to 18 carbon atoms.

5. The process according to claim 4 wherein the molar ratio of component (ii) to component (i) is about 1 to 1.5.

6. The process of claim 5 wherein said complex is used in a quantity of about 0.001 to 0.5 mole percent based on the moles component (i) and the moles of polyisocyanate or mixture of polyisocyanate and monoisocyanate to be trimerized.

7. The process of claim 4 which comprises conducting the trimerization reaction at a temperature of about 10° to 100° C.

8. The process of claim 6 which comprises conducting the trimerization reaction at a temperature of about 10° to 100° C.

9. The process of claim 3 wherein the hydroxyl groups of the at least one monovalent or higher valent polyether alcohol are blocked with blocking agents.

10. The process according to claim 1, characterized in that the complex used as trimerization catalyst is added to the polyisocyanate to be trimerized in the form of a solution in a solvent which is inert towards isocyanate groups or in the form of a solution in a liquid containing isocyanate reactive groups.

11. A process for the production of polyurethanes which comprises
   (a) preparing an isocyanate component according to the process of claim 1, and
   (b) reacting said isocyanate component with an isocyanate-reactive component.

12. A process for the production of polyurethanes which comprises
   (a) preparing an isocyanate component according to the process of claim 8, and
   (b) reacting said isocyanate component with an isocyanate-reactive component.

* * * * *